United States Patent [19]

Pancham et al.

[11] Patent Number: 4,470,969
[45] Date of Patent: Sep. 11, 1984

[54] PROCESS FOR PRODUCING A CONCENTRATE OF COAGULATION FACTORS VII AND VIIA

[75] Inventors: Nazreen Pancham, San Francisco; Timothy Zuffi, El Cerrito, both of Calif.

[73] Assignee: Miles Laboratories, Inc., Elkhart, Ind.

[21] Appl. No.: 557,579

[22] Filed: Dec. 2, 1983

[51] Int. Cl.$^3$ ............................................. A61K 35/16
[52] U.S. Cl. ................................. 424/101; 260/112 B
[58] Field of Search ...................... 424/101; 260/112 B

[56] References Cited

U.S. PATENT DOCUMENTS 4,357,321  11/1982  Thomas .............................. 424/101

OTHER PUBLICATIONS

Chem. Abst., 10th Collect. Index, vols. 86-95, (1977-1981), Chem. Subst., pp. 10380CS & 10381CS.

*Primary Examiner*—Sam Rosen
*Attorney, Agent, or Firm*—Lester E. Johnson

[57] ABSTRACT

There is disclosed a process for producing coagulation factors VII and VIIa in relatively high purity by contacting an aqueous preparation containing factors VII and VIIa with a protein precipitant and separating the coagulation factors and other proteins therefrom, contacting the resulting solution with a divalent metal salt adsorbent having selective affinity for calcium-binding coagulation factors and eluting the coagulation factors therefrom, and contacting the eluate with an anionic exchange resin and selectively eluting coagulation factors VII and VIIa therefrom by step or gradient elution techniques to obtain factors VII and VIIa free of other coagulation factors and other proteins.

10 Claims, No Drawings

PROCESS FOR PRODUCING A CONCENTRATE OF COAGULATION FACTORS VII AND VIIA

BACKGROUND OF THE INVENTION

1. Field of the Invention

This invention relates to the blood coagulation components Factors VII and VIIa, and to a process for producing a blood coagulation promoting product containing Factors VII and VIIa in relative purity and free from other coagulation factors.

2. Description of the Prior Art and Related Art

Polson, U.S. Pat. No. 3,415,804, discloses, as an alternative to the alcohol fractionation method, a process for fractionating mixtures of proteinaceous substances in aqueous medium with polyethylene glycol used as a dispersibility depressant resulting in a single liquid phase containing one fraction in dispersion and a solid phase fraction of a composition different from that of the original mixture. Selectivity can be achieved according to the patent by increasing the concentration of the precipitant and by control of the pH during precipitation.

Fekete et al, U.S. Pat. No. 3,560,475, discloses a method for producing a prothrombin complex, containing factors II, VII, IX and X, by suspending Cohn plasma fractions containing the factors in saline, mixing the supernatant with tribasic calcium phosphate at a pH of 6.8 to 7.2 to adsorb the factors, mixing the adsorbed protein precipitate with 0.05 to 0.2M trisodium citrate, and subjecting the resulting supernatant to two successive polyethylene glycol precipitations first at 5-10% and pH 6.8 to 8.0 and then at least at 20% and pH 5.0-5.4, with retention of the resulting precipitate as the prothrombin complex.

Thomas, U.S. Pat. No. 4,287,180 discloses a method for treating a patient having an inhibitor of blood clotting factors by administering to the patient a therapeutically effective dose of an aqueous composition including, in units/ml, factor VIII correctional activity, about 2-35; prothrombin, about 1-10; thrombin, less than 0.003; factor VII, about 37-190; factor VIIa, about 8-80; factor IX, about 15-112; factor IX precursor, 0-30; factor X, about 1-30; and factor Xa, about 1-10.

Thomas, U.S. Pat. No. 4,357,321, a division of U.S. Pat. No. 4,287,180 mentioned above, discloses a method for treating a patient having an inhibitor of blood clotting factor by administering to the patient a therapeutically effective dose of an aqueous composition of 37-110 units/ml of factor VII and 8-80 units/ml of factor VIIa.

In both of the foregoing Thomas patents, there is disclosed the use of Cohn plasma fractions I+II+III, I and III, II and III, III, III-0, IV-1, or IV-1 and IV-4. IV-1 is the preferred fraction and is disclosed in the working examples. The starting compositions are dissolved in a buffer or saline to a concentration of about 10% weight/volume at about 20° C., screened for clotting factor activity to determine the degree of preexisting spontaneous activation, partially purified by adsorption onto a suitable, known prothrombin complex adsorbent (e.g. tribasic calcium phosphate or a diethylaminoethyl group substituted resin), followed by elution from the adsorbent in a volume of about 4% of the volume of the dissolved Cohn fraction, none of the volumes or temperatures being critical. Example 1 of the patent illustrates a typical manufacturing run for the preparation of an activated PCC (prothrombin complex) according to the invention of the patent wherein the starting material, a Cohn fraction IV-1 paste, is suspended in saline at a pH of 7.2; a resultant precipitate is allowed to settle; and a clear supernatant is obtained by centrifugation. Then calcium phosphate is added to the supernatant, the calcium phosphate adsorbed coagulation factors are recovered, the factors separated from calcium phosphate by vigorous mixing with a volume of 0.1M sodium citrate equal to 4% of the dissolved paste, and the resulting suspension is centrifuged and the supernatant is recovered. Following this, the coagulation factors in the supernatant are activated by contacting the supernatant with silica and the activated PCC is further purified by PEG precipitation steps followed by dissolution of the precipitate in 0.02M sodium citrate, sterile filtration and lyophilization.

Thomas, U.S. Pat. No. 4,382,083 and PCT publication WO 83/00016 which corresponds thereto, disclose a method for treating a patient having a clotting factor defect by administering a composition of an effective hemostatic amount of factor VIIa, which composition is uncontaminated by other activated blood clotting factors having sufficient activity alone to produce a hemostatic effect. Unactivated precursor forms of factors may be present in the compositions and the amounts of unactivated factors II, VII, IX and X typically range from about 1-10, 20-250, 0-30, and 1-30 units/ml, respectively. Preferably, the compositions are essentially free of factors IX and II but contain factors VII and/or X in the above concentrations. Suitable factor VIIa compositions for use according to the patented method can be produced according to the methods of Kisiel et al, *Biochemistry*, 16 (9), 4189 (1977) or Broze and Majerus, *J. Biol. Chem.*, 255, 1242 (1980).

Kisiel et al, supra, disclose a 5-step procedure to isolate and purify factor VII from bovine plasma which involves barium sulfate adsorption and elution, DEAE Sephadex ® batchwise adsorption and elution, benzamidine-agarose column chromatography, heparin-agarose column chromatography, and preparative polyacrylamide gel disc electrophoresis.

Broze and Majerus, supra, disclose the purification of human factor VII from human, citrated, fresh frozen plasma with platelets removed by barium citrate adsorption and elution and ammonium sulfate fractionation. The resulting solution was then treated to two successive QAE-Sephadex chromatographic purification steps followed by gel filtration on Sephadex G-100.

Bajaj et al, *J. Biol. Chem.*, 356 (1), 253 (1981), disclose the purification of human factor VII from blood plasma using barium citrate adsorption, ammonium sulfate fractionation, DEAE-Sephadex chromatography, preparative polyacrylamide gel electrophoresis (PAGE), and SDS-PAGE.

Gladhaug et al, *Biochim. Biophys. Acta*, 215, 105 (1970), disclose the purification of factors VII and X from human serum using barium sulfate-Sephadex, DEAE-Sephadex, polyacrylamide gel filtration, and polyacrylamide gel disc electrophoresis.

Current thinking in the field to which this invention pertains is that there are two separate systems—intrinsic and extrinsic—which can promote clotting and can thereby participate in normal hemostasis. In factor VIII deficient persons, who also have circulating antibodies to the molecule, replacement therapy with factor VIII concentrates has been shown to be of limited or of no value, presumably because the intrinsic system in such persons has been largely inhibited. Treatment with prothrombin complex products, however, has had varying degrees of success in these patients; but the active principal in these materials has not, as yet been elucidated. It is not unlikely that these products function by simply enhancing the contribution of the extrinsic system to clotting, taking into consideration that they contain concentrated amounts of some of the extrinsic system enzymes, namely, factors II, VII and X, more specifically, these products may function as follows: Factor VII/VIIa levels are raised to the extent that appreciable levels of tissue factor VII/VIIa complex are formed. This complex can interact with both of factors IX and X and, if this occurs, a series of activations can arise. Activated factor X is shown to be able to activate factor VII and factor IX reciprocally, to be autoactivatable, and to activate factor II. The net effect of any of these reactions would thus be a great increase of factor Xa and, hence, factor IIa activity, which would further result in subsequent clot formation.

Crucial to the above-described scheme is the concept that the activation remains localized to prevent systemic, uncontrolled clot formation. Under normal conditions, this danger is avoided probably because tissue factor may be fairly selectively exposed at the site of injury keeping the activations within a local environment and also because of the presence of circulating, naturally occurring protease inhibitors.

That activation can occur at all in the presence of these circulating inhibitors, even in a local environment, may be due to the reciprocal activations of factors VII, IX and X. Although it is generally accepted that the extrinsic system can function as described at least in vitro, it is not understood why the extrinsic system does not control bleeding in factor VIII deficient persons. It is conceivable that the extrinsic system under normal circumstances acts only as an auxiliary to the intrinsic system to promote clotting. While it may be that the levels of extrinsic system participants are high enough to repair certain kinds, or limited amounts of, physiologic damage, they may not be sufficient to correct the major bleeding episodes that occur in factor VIII or IX deficiencies. According to the above, factor VII would be a requirement in order for the described reciprocal activations to occur.

There is a need, then, for a process to produce factor VII and factor VIIa in relatively pure form, free of the other factors, II, IX and X, with which factors VII and VIIa are generally associated and isolated, for both experimental and therapeutic purposes.

SUMMARY OF THE INVENTION

This invention is a process for producing a concentrate containing factors VII and VIIa in relative purity, free of factors II, IX and IXa, and X and Xa, from sources including human plasma proteins and plasma protein fractions. In another aspect, this invention is a pharmaceutical preparation consisting essentially of the concentrate containing factors VII and VIIa produced according to the process of the invention.

DETAILED DESCRIPTION OF THE INVENTION

This invention is a process for producing a concentrate consisting essentially of blood coagulation factors VII and VIIa and having a specific activity in the range of about 500 to 3000 u/$A_{280}$ consisting essentially of the steps of:

(a) contacting an aqueous preparation, in the form of a solution or suspension, of plasma proteins containing factors VII and VIIa, at a temperature of about 4° to 25° C. and at a pH of about 4 to 9 and in the presence of a suitable buffer to maintain the pH at about 4 to 9, with about 1 to 10% (weight-/volume, based on total weight of plasma proteins) of polyethylene glycol having a molecular weight of about 200 to 20,000 to precipitate from the preparation PEG-precipitable proteins and the other insoluble matter present in the aqueous preparation to obtain an aqueous supernatant containing factors VII and VIIa separated from the PEG-precipitable proteins and insoluble matter;

(b) contacting the aqueous supernatant from step (a), adjusted to a pH of about 6 to 8, with an adsorbent having selective affinity for calcium-binding proteins, including factors II, VII, IX and X, selected from the group of water-insoluble divalent metal salts, to adsorb the calcium-binding proteins;

(c) selectively eluting, by techniques selected from step and gradient elution techniques, factors II, VII and VIIa, IX and IXa, and X and Xa from the protein-bound adsorbent from step (b) by the addition of a buffer solution containing suitable soluble salts effective to displace the bound proteins and collecting the eluate pool;

(d) contacting the eluate pool from step (c), adjusted to a pH of about 3 to 11, with an anionic exchange resin having affinity for the calcium-binding proteins, including factors II, VII and VIIa, IX and IXa, and X and Xa, and adsorbing thereon the calcium-binding proteins; and (e) selectively eluting, by techniques selected from step and gradient elution techniques, factors VII and VIIa from the protein-bound adsorbent from step (d) by the addition of a buffer solution containing suitable salts in increasing ionic strength.

The polyethylene glycol precipitant used in step (a) is a high molecular weight polymer generally produced by reacting ethylene oxide with ethylene glycol or with water to obtain the polycondensation product having repeating oxyethylene groups between a terminal hydroxyl group and a terminal hydroxyethyl group. The polyethylene glycol, sometimes abbreviated "PEG", can range in molecular weight from about 200 to 20,000, preferably about 2,000 to 10,000, more preferably about 4,000 to 8,000, most preferably about 6,000, and is used at a concentration in the range of 1 to 10% (w/v, based on total weight of plasma proteins), most preferably about 2 to 5% (w/v). The temperature in step (a) can range from the cold, 4° C., to room temperature, about 25° C. As an example of a suitable buffer useful in step (a), there may be mentioned the class of Good buffers including TRIS® buffers (TRIS® is tris(hydroxymethyl) aminomethane) and morpholino ethane sulfonate (MES) and citrate, which will generally be used in combination with another buffer such as saline.

The amount of PEG, 2–5%, was found to be most preferred because this was the least amount of PEG required to obtain a clear supernatant and also acceptable factor VII/VIIa recovery. Total factor VII/VIIa activity was found not to vary at 2–5% PEG with PEG molecular weight ranging between 4,000–8,000, particularly 4,000–6,000. Step (a) can be carried out conveniently at pH 7.5. The use of about 0.15–0.3M NaCl in the plasma protein preparation for PEG precipitation was advantageous to keep the proteins in solution and to obtain the highest possible specific activity of factor VII/VIIa.

The adsorbent having selective affinity for calcium-binding proteins used in step (b) preferably is selected from any member of the water-insoluble divalent metal salts, preferably these salts wherein the divalent metal is calcium, magnesium or barium and wherein the anion is phosphate, sulfate or citrate. Other adsorbents which may be used in place of the water-insoluble divalent metal salt include polysaccharide adsorbents such as those which are used in step (d). Step (b) may be conveniently carried out using column or batch chromatographic techniques. Most preferably, the water-insoluble divalent metal salt is tricalcium phosphate, whose common name is hydroxyapatite. The process of the invention can be conveniently carried out using, in step (b), a preferred pH of 5 to 8.

As an example of a suitable buffer in step (c), there may be mentioned MES and TRIS buffers and as a suitable salt there may be mentioned sodium phosphate.

The anionic exchange resin adsorbent used in step (d) is preferably a polysaccharide adsorbent selected from the group of polygalactose, polydextran and cellulose resins wherein the polysaccharide chains have positively charged groups, e.g. diethylaminoethyl groups or quaternary ethyl amino groups attached to the glucose units in the polysaccharide. Examples of suitable polysaccharide adsorbents, as the anionic exchange resin, include commercially available anionic exchange resins such as DEAE-Sepharose, DEAE-Sephadex and DEAE-cellulose. Most preferably, the anionic exchange resin is DEAE-Sepharose. Step (d) may be conveniently carried out using column or batch chromatographic techniques wherein the adsorbent, for example, DEAE-Sepharose, is equilibrated in MES-saline. It is known in the art that the conditions of ion exchange in step (e) is temperature dependent. The temperature is not critical and can be in the range of about 4° C.–25° C. For example, at room temperature (about 25° C.), the ionic strength of the salt may be in the range of 0.1–0.4M. As an example of a suitable salt useful in the selective elution step there may be mentioned sodium chloride. A preferred pH for step (d) is 5 to 8 for convenience.

As the starting protein solution or suspension, there may be used any material containing coagulation factors VII and VIIa. This may include plasma and plasma fractions, media taken from the culture of microorganisms, and the like. The starting material may, and usually will, also contain one or more of factors II, IX and X, and may further contain factors XI and XII. Generally, the starting material will be solutions or suspensions of Cohn plasma fractions I+II+III, I+III, II+III, III, III-0, IV-1, or IV-1+IV-4. Preferably, the starting material is selected from Cohn fractions III and IV-1. The starting material is generally dissolved or suspended in distilled water, or buffer solution or saline solution and may be present at a concentration in the broad range of 1 to 80% (weight/volume, w/v), preferably about 2 to 50% (w/v), more preferably about 5 to 20% (w/v), and most preferably about 8 to 15% (w/v). Especially preferred, for convenience, is a starting material concentration of 10% (w/v).

The particular advantage of the process of this invention arises from the initial treatment, to remove PEG-precipitable proteins and other insoluble matter from the starting material, which has been found to provide for enhanced efficiency in the selective binding of factors VII/VIIa in the subsequent purification steps, especially using column chromatographic techniques, and in subsequent selective step or gradient elution steps which are conventional in the art to which the invention pertains.

This invention permits more facile removal and separation of substances which are undesired and which constitute contaminants in the product concentrate containing factors VII and VIIa.

Another of the advantages as will be recognized by those skilled in the art is that the invention permits the recovery of other coagulation factors, including factors II, IX and X and activated forms thereof, free of factors VII and VIIa by further gradient elution in step (e) using a buffer solution containing higher and increasing ionic strength.

The eluate containing factors VII and VIIa obtained in step (e) may then be processed to put it in condition for use. Generally, the eluate is concentrated to reduce its water content by conventional means, for example, by ultrafiltration. Also, the residual salt content in the eluate may be reduced by conventional means, for example, dialysis, diafiltration and the like. The resulting concentrate containing factors VII and VIIa is suitable for use as a pharmaceutical preparation for therapeutic purposes and for experimental purposes. The pharmaceutical preparations may contain any of the conventional pharmaceutical adjuvants and excipients. The pharmaceutical preparations intended for therapeutic use should contain a therapeutically effective amount of factors VII and VIIa, that is, that amount necessary for preventative or curative purposes.

The pharmaceutical preparations comprising the product produced by the process of the invention may be treated using conventional procedures to reduce and eliminate infectious microorganisms and to render the preparations non-viral, particularly non-hepatitis, infective. The pharmaceutical preparations may be sterile-filtered, heat treated, chemically treated, subjected to ultraviolet radiation or treated on colloidal silica. For example, the preparations, in wet or dry state (that is, as the concentrate itself or freeze-dried), may be heated at temperatures of about 60° to 85° C. for a period of several minutes to several days as may be required, generally in the presence of a heat stabilizing agent. Suitable stabilizing agents include nonpolar anions with molecular weights greater than 80, sugars, reduced sugars, and amino acids. Examples of suitable nonpolar anions include salts of carboxylates, hydroxycarboxylates and amino acids such as a sodium or potassium caprylate, caprate, oleate, laurate, valerate, acetylphenylalaninate, acetyleucinate, and acetyltryptophanate. Examples of suitable sugars include glucose, sucrose and maltose to name but a few, and examples of suitable reduced sugars include erythritol and mannitol. Examples of suitable amino acids include lysine, glysine, proline and glutamic acid to name but a few. By way of example without limitation, suitable conventional known processes to reduce or eliminate infectious microorganisms and render the preparations non-viral infective include those disclosed in U.S. Pat. Nos. 3,041,242, 3,057,781, 3,227,626, 4,061,735, 4,137,307, 4,297,344, 2,705,230, 2,897,123, 3,284,301, 3,454,929, 4,379,085 and 4,370,264, and European Patent Publication 0058993, and in references disclosed in the patents.

The following examples illustrate but a few embodiments of the present invention and are not to be construed as limiting in scope. All parts and percentages are by weight and temperatures in degrees Celsius unless otherwise indicated.

Characterization of Factor VII/VIIa

Factor VII clotting activity is assayed by the Owren one-stage method using the specific factor-deficient plasma and rabbit-brain thromboplastin containing calcium.

See Owren, P. A. (1949). A quantitative one-stage method for the assay of prothrombin. Scand. J. Clin and Lab. Investigation, 1, 81.

The degree of activation of factor VII is determined by comparing the total clotting activity of f. VII/VIIa with the amidolytic activity of f. VII (the amidolytic activity is insensitive to the state of activation of f. VII) and taking a ratio f. VIIc/f. VIIam The amidolytic assay is performed according to the published procedure of Seligsohn et al, Blood, Vol, 52, No. 5 (November), 1978.

were pooled, concentrated and buffer was exchanged for the next step.

In the case of batch adsorption, stepwise elution of factor VII/VIIa was obtained with equilibrating buffer washes containing increasing amounts of sodium phosphate.

Steps (d) and (e)

The pool containing factor VII/VIIa activity was adsorbed onto DEAE-Sepharose (in a column) equilibrated with 0.02 MES buffer, pH 6.0. Factor VII/VIIa was eluted with a gradient consisting of equilibrating buffer containing 0.1M NaCl in the mixing beaker and equilibrating buffer containing 0.4M NaCl in the reservoir. Factor VII activity eluted between 0.15M and 0.35M NaCl.

The factor VII/VIIa thus prepared was essentially free of other clotting activity, e.g., factor II, IX, X. Trace amounts of activated forms of these clotting factors were evident if insufficient amounts of proteolyte inhibitors were employed during purification.

The results are summarized in the accompanying Table.

| Step | Recovery of Factor VII/VIIa Clotting Activity From 100 grams* Fraction III | | | |
|---|---|---|---|---|
| | Total F. VII/VIIa Clotting Units | % Recovery | Specific Activity | Degree of Activation F. VIIc/F. VII AM |
| PEG Supernatant (Fr. III) | 38,800 | 100 | 2.5 | 30–40 Fold |
| Post Hydroxyapatite (Column Chromatography) | 24,500 | 63* | 167-5 | 50–60 |
| Post DEAE | 14,300 | 37 | 1059 | about 50 |

*Batch adsorption and elution in one run yielded about 69%.

Factor VII, when activated, is thought to increase clot formation by approximately 50 fold over the native f. VII.

EXAMPLE 1

Step (a)

100 g. of Cohn Fr. III was suspended in 0.5M Tris, 0.15M-. NaCl, pH 7.5 buffer, 4° C., to make a 10% solution. The suspension was mixed for about 1 hour. PEG 6000 powder was added to a final concentration of 3% (weight/volume). The mixture was stirred for ½ hour at 4° C. then centrifuged and the supernatant collected.

Factor VII clotting activity in the supernatant was 40 units/ml. $A_{280}$ was 16 units/ml.

Steps (b) and (c)

The supernatant was adsorbed onto tri-calcium phosphate (Hydroxylapatite ®—Bio-Rad) (either in a column mode or batchwise) which was equilibrated with 0.05M Tris, 0.15M NaCl, pH 7.5 buffer. This step was done at room temperature for convenience, but can be done at 4° C. The ratio of swollen resin to sample volume was about 5%. At this ratio virtually all of the factor VII activity is adsorbed. The resin is then washed with equilibrating buffer (several bed volumes) followed by equilibrating buffer containing 1M NaCl. F. VII/VIIa activity was eluted with a phosphate gradient in the case of column chromatography. The mixing chamber contained equilibrating buffer, no phosphate; reservoir contained equilibrating buffer plus 0.35M sodium phosphate. Factor VII/VIIa activity eluted between 0.15 and 0.3M phosphate concentration. Fractions containing peak factor VII/VIIa clotting activity

What is claimed is:

1. A process for producing a concentrate consisting essentially of blood coagulation factors VII and VIIa and having a specific activity in the range of about 500 to 3000 $u/A_{280}$ consisting essentially of the steps of:

(a) contacting an aqueous preparation, in the form of a solution or suspension, of plasma proteins containing factors VII and VIIa, at a temperature of about 4° to 25° C. and at a pH of about 4 to 9 and in the presence of a suitable buffer to maintain the pH at about 4 to 9, with about 1 to 10% (weight/volume, based on total weight of plasma proteins) of polyethylene glycol having a molecular weight of about 200 to 20,000 to precipitate from the preparation PEG-precipitable proteins and other insoluble matter present in the aqueous preparation to obtain an aqueous supernatant containing factors VII and VIIa separated from the PEG-precipitable proteins and insoluble matter;

(b) contacting the aqueous supernatant from step (a), adjusted to a pH of about 6 to 8, with an adsorbent having selective affinity for calcium-binding proteins, including factors II, VII, IX and X, selected from the group of water-insoluble divalent metal salts, to adsorb calcium-binding proteins;

(c) selectively eluting, by techniques selected from step and gradient elution techniques, factors II, VII and VIIa, IX and IXa, and X and Xa from the protein-bound adsorbent from step (b) by the addition of a buffer solution containing suitable soluble salts effective to displace the bound proteins and collecting the eluate pool;

(d) contacting the eluate pool from step (c), adjusted to a pH of about 3 to 11, with an anionic exchange resin having affinity for the calcium-binding proteins, including factors II, VII and VIIa, IX and IXa, and X and Xa, and adsorbing thereon the calcium-binding proteins; and (e) selectively eluting, by techniques selected from step and gradient elution techniques, factors VII and VIIa from the protein-bound adsorbent from step (d) by the addition of a buffer solution containing suitable salts in increasing ionic strength.

2. A process according to claim 1 wherein the anionic exchange resin used in step (d) is a polysaccharide adsorbent selected from the group of polygalactose, polydextran and cellulose resins wherein the polysaccharide chains have positively charged groups selected from diethylaminoethyl groups and quaternary ethyl amino groups attached by to the glucose units in the polysaccharide.

3. A process according to claim 1 wherein the plasma protein is selected from Cohn fractions III and IV-1 and wherein the plasma protein is present in a concentration in the range of about 1 to 80% (weight/volume).

4. A process according to claim 1 wherein the volume of the eluate from step (e) is reduced by ultra-filtration.

5. A process according to claim 1 including the further step of treatment to render the eluate from step (e) non-viral infective and to reduce or eliminate infectious microorganisms.

6. A process according to claim 4 including the further step of treatment to render the eluate from step (e) non-viral infective and to reduce or eliminate infectious microorganisms.

7. A process for producing a concentrate consisting essentially of blood coagulation factors VII and VIIa and having a specific activity of about 500 to 3000 u/$A_{280}$ consisting essentially of the steps of:

(a) contacting an aqueous preparation, in the form of a solution or suspension, of plasma proteins selected from Cohn fraction III and Cohn fraction IV-1, containing coagulation factors II, VII, IX and X, at a temperature of about 4° to 25° C. and at a pH of about 6 to 9 and in the presence of a suitable buffer to maintain the pH of the preparation at about 6 to 9, with 3% polyethylene glycol having a molecular weight of about 6,000 to precipitate from the preparation PEG-precipitable proteins and other insoluble matter present in the aqueous preparation to obtain an aqueous supernatant containing factors VII and VIIa separated from the PEG-precipitable proteins and insoluble matter;

(b) contacting the supernatant from step (a), adjusted to a pH of about 5 to 8, with tricalcium phosphate (hydroxyapatite) to adsorb thereon the calcium-binding coagulation factors II, VII, IX and X;

(c) selectively eluting, by gradient elution techniques, factors II, VII, IX and X, and of activated factors present, VIIa, IXa and Xa, from the protein-bound adsorbent from step (b) by the addition of a buffer solution containing soluble salts effective to displace the bound proteins and collecting the eluate pool;

(d) contacting the eluate pool from step (c), adjusted to a pH of about 5 to 8, with an anionic exchange resin selected from the group of polygalactose, polydextran and cellulose wherein the polysaccharide chains have diethylaminoethyl groups attached to the glucose units in the polysaccharide; and (e) selectively eluting, by gradient elution techniques, factors VII and VIIa from the protein-bound adsorbent from step (d) by the addition of a buffer solution containing suitable salts in increasing ionic strength.

8. A process according to claim 7 wherein the volume of the eluate from step (e) is reduced by ultra-filtration.

9. A process according to claim 7 including the further step of treatment to render the eluate from step (e) non-viral infective and to reduce or eliminate infectious microorganisms.

10. A process according to claim 8 including the further step of treatment to render the eluate from step (e) non-viral infective and to reduce or eliminate infectious microorganisms.

* * * * *